United States Patent [19]

Akcelrod

[11] Patent Number: 4,940,218
[45] Date of Patent: Jul. 10, 1990

[54] ORTHOPEDIC OPERATING TABLE FOR LIMBS, AND IN PARTICULAR FOR THE LOWER LIMBS

[75] Inventor: Patrick Akcelrod, Sens, France
[73] Assignee: Societe Anonyme dite: Etablissements Tasserit, Gron, France
[21] Appl. No.: 232,986
[22] Filed: Aug. 17, 1988
[30] Foreign Application Priority Data
  Oct. 5, 1987 [FR] France ................ 87 13708
[51] Int. Cl.⁵ ............................. A61G 13/00
[52] U.S. Cl. .......................... 269/322; 269/328
[58] Field of Search ................ 269/322–328, 269/71, 75

[56] References Cited

U.S. PATENT DOCUMENTS

| | | | |
|---|---|---|---|
| 2,073,932 | 3/1937 | Hawley | 128/71 |
| 2,150,314 | 3/1939 | Bell | 128/84 |
| 2,590,739 | 3/1952 | Wagner et al. | 128/84 |
| 3,766,384 | 10/1973 | Anderson | 250/446 |
| 4,568,071 | 2/1986 | Rice | 269/322 |

OTHER PUBLICATIONS

"Tables by Tower", Roger Anderson, Feb. 1951.

Primary Examiner—Judy Hartman
Attorney, Agent, or Firm—Sughrue, Mion, Zinn, Macpeak & Seas

[57] ABSTRACT

The present invention relates to orthopedic operating tables. The table of the invention includes a stand (1) suitable for being positioned on ground (2), a base (4) mounted on the stand, and a support flap (7, 8) for supporting the trunk of a patient, the flap is connected to the base. A beam (18, 19) is pivotally mounted to the base in the proximity of the point where a person's limb joins at the trunk, with the beam being made of a material which is transparent to radiographic radiation, and the distance between the beam and the ground when the beam extends substantially parallel to the ground is greater than the height of the source required for emitting radiographic radiation from the ground. The table is particularly suitable for resetting fractures or the like on the lower limbs of a patient.

9 Claims, 2 Drawing Sheets

ORTHOPEDIC OPERATING TABLE FOR LIMBS, AND IN PARTICULAR FOR THE LOWER LIMBS

The present invention relates to tables enabling operations to be performed on patients suffering in their limbs, for example from fractures which it is absolutely essential to reset under the best possible conditions, said tables being more particularly adapted to operating on the lower limbs.

BACKGROUND OF THE INVENTION

Orthopedic operating tables, in particular for operating on the lower limbs, already exist which enable surgeons to operate under relatively comfortable conditions. These tables are generally constituted by a relatively large stand suitable for fixing on the ground. The top of the stand supports a base on which one or two flaps are generally fixed offset from one of the sides of the base for the purpose of supporting the trunk and the head of the patient. On its side opposite to the side supporting the flaps, the base supports two beams articulated substantially about two points situated at a relatively short distance from each other, said beams being generally longer than the lower limbs of a person and serving to carry, inter alia auxiliary elements suitable, for example, for fixing the feet and possibly intermediate bearing surfaces for holding the leg at the knee, given that these bearing surfaces must be capable of being displaced along the beams substantially between their two ends.

Such a table also includes, a pelvis support which is generally positioned on the base and which serves to hold the pelvis of the patient and also to position the crutch at a well-determined reference point which is fixed relative to the base so as to enable the surgeon to position and align each limb of the patient properly prior to resetting the fractures as well as possible, so that the patient will be able to use the fractured limb(s) in their original configuration after healing.

However, these operations become more complicated when it is necessary in difficult cases to perform the operation with radiographic assistance, and more particularly when continuous radiographic monitoring is required. In order to perform operations under such conditions, the table is associated with a source emitting radiographic radiation (generally X-rays) and a receiver for receiving the radiation emitted by the source, of the scintilation camera type, suitable for processing and scanning the received image and, optionally, of displaying it on a video screen, for example. Adding such items to an operating table considerably increases the bulk of the structure overall and the surgeon must operate under more cramped conditions.

During such operations, it is necessary to dispose the pair of radiographic items, i.e. the source of radiation and the receiver, in such a manner as to ensure they are positioned as well as possible relative to each other and relative to the limb being examined. Unfortunately, the table support or a table-raising platform, together with the beams and associated apparatuses, constitute numerous obstacles which get in the way of and limit the extent to which these two items can be moved in translation or rotation.

THe object of the present invention is to mitigate the above-mentioned drawbacks and to provide an orthopedic operating table, in particular for the lower limbs, which enables a surgeon to operate under optimum ease-of-use conditions, and which together with the various associated items such as a source of radiographic radiation and its receiver constitute an assembly which takes up as little room as possible.

SUMMARY OF THE INVENTION

The present invention provides an orthopedic operating table for the limbs of a person, in particular the lower limbs, the table comprising:

a stand suitable for being positioned on the ground;

a base mounted on the top of said stand;

at least one flap for supporting the trunk of said person;

support means for attaching said flap to said base so that said flap is offset relative to said base;

at least one beam comprising a central portion in the form of a hollow circularly cylindrical tube made of a material which is transparent to radiographic radiation emitted by a radiation source;

means for mounting said beam pivotally to said base in the proximity of the point where said limb joins the trunk of the person, and on the opposite side of the base to the side on which the support means for said flap are disposed with the distance between said beam when in its position substantially parallel to said ground on which said stand is suitable for being positioned and said ground being greater than the height of the source of radiographic radiation or of the radiographic image receiver, said means for mounting said beam pivotally to said base comprising a projecting portion fixed to said base and a ball-and-socket joint whose male portion is constituted by a convex spherical portion fixed to said projecting portion of the base by a lug, and whose female portion is constituted by an end piece fixed to a first end of said beam, the inside of the said end piece being shaped to include a complementary concave hemispherical portion forming a half-cup including an opening through which said connection lug passes; and controllable locking means for locking said ball-and-socket joint in a determined position constituted by a brake shoe disposed in the proximity of the convex portion and including a friction material on its face facing the convex portion, a transmission rod constituted by a circularly cylindrical hollow tube made of a material transparent to the radiographic radiation, with a first end of said rod cooperating with said shoe and with its second end emerging from the end of the tubular portion of said beam, and means for controlling the displacement of said transmission rod relative to said tubular portion forming said beam.

The present invention also provides an orthopedic operating table for the limbs of a person, in particular the lower limbs, the table comprising:

a stand suitable for being positioned on the ground;

a base mounted on the top of said stand;

at least one flap for supporting the trunk of said person;

support means for attaching said flap to said base so that said flap is offset relative to said base;

at least one beam;

means for pivotally mounting a first end of said beam to said base in the proximity of the point where said limb joins the trunk of the person, and on the opposite side of the base to the side on which the support means for said flap, said beam being made of a material which is transparent to radiographic radiation emitted by a radiation source, the distance between said beam when in its position substantially parallel to said ground on which said stand is suitable for being positioned and said ground being greater than the height of the source of radiographic radiation or of the radiographic image receiver, said beam comprising, at its second end, means for supporting and holding a foot of the patient, said means comprising a support rod, a boot fixed to one end of said rod and suitable for imprisoning a foot of the patient, and a deformable parallelogram connecting said rod to said beam, said parallelogram being constituted by fixing lugs, with the ends of said lugs being pivotally mounted respectively on said second end of said beam and on said support rod; and a control link for controlling said deformable parallelogram, said control link being pivotally mounted at its two ends respectively on a portion of said base and on a projecting portion of a lug forming said parallelogram, such that the points of rotation of said ball-and-socket joint, of the lug on the beam, of the link on the lug, and of the link on the base lie on the vertices of a trapezium, with the length of said link between its two points of rotation being greater than the length of said beam between said two points of rotation, said link and the tubular portion constituting the beam being situated on either side of a plane substantially perpendicular to said ground on which said stand is suitable for being positioned.

The present invention also provides an orthopedic operating table for the limbs of a person, in particular the lower limbs, the table comprising:

a stand suitable for being positioned on the ground;
a base mounted on the top of said stand;
at least one flap for supporting the trunk of said person;
support means for attaching said flap to said base so that said flap is offset relative to said base;
at least one beam;
means for pivotally mounting said beam to said base in the proximity of the point where said limb joins the trunk of the person, and on the opposite side of the base to the side on which the support means for said flap, said beam being made of a material which is transparent to radiographic radiation emitted by a radiation source, the distance between said beam when in its position substantially parallel to said ground on which said stand is suitable for being positioned and said ground being greater than the height of the source of radiographic radiation or of the radiographic image receiver; and a pelvis support situated in the half-space delimited by the plane passing through the point of rotation of said beam and substantially perpendicularly to the ground on which said stand is suitable for being positioned, and including said beam, said pelvis support being constituted by a thin wall shaped to receive the pelvis of a patient, said thin wall being laterally reinforced by thin sides extending obliquely relative to the normal to said thin wall, said pelvis support being made of a material which is transparent to radiographic radiation.

BRIEF DESCRIPTION OF THE DRAWINGS

Embodiments of the invention are described by way of example with reference to the accompanying drawings, in which.

Naturally, similar items shown in FIGS. 1 to 6 belonging to a common embodiment are designated in all of the figures by the same references, regardless of which figure they are shown in.

MORE DETAILED DESCRIPTION

Figure 1:
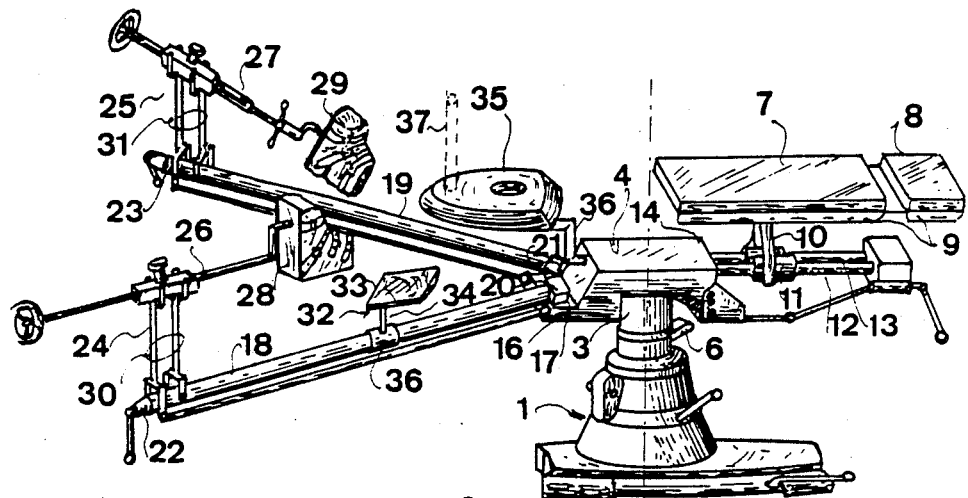
FIG. 1 is a perspective view of an embodiment of an orthopedic operating table in accordance with the invention.

FIG. 1 is a perspective view of an embodiment of an orthopedic operating table more particularly suitable for operating on the lower limbs of a patient. This table comprises a stand 1 suitable for taking up a firm position on the ground 2. The top 3 of the stand supports a solid base 4 which is generally pivotably mounted about a vertical axis 5, for example by means of a ball bearing structure, or the like. In addition, the bearing may be locked by any appropriate means, for example a brake having a control lever 6 which is visible in the figure. Such locking means are easily implemented by the person skilled in the art and are not described in greater detail herein.

The table includes at least one flap, and in the present example two flaps 7 and 8 which are generally mounted on a common tray 9 which is itself mounted on lugs 10. The lugs 10 are generally slidably mounted by means of sleeves 11 mounted on two slide bars 12 and 13. The slide bars are fixed to the side portion 14 of the base 4. As above, the sleeves 11 can be locked in any selected position on these two slide bars. Here again, the locking means are easily implemented and are not described in greater detail. Thus, the two flaps 7 and 8 may be positioned relative to the above-defined axis 5 by being moved in translation along the two side bars 12 and 13 for the purpose of supporting the trunk and the head of the patient, with these two flaps having dimensions adapted to the dimensions of the parts of the patient's body that they are to support.

The side 16 of the base 4 opposite to the side 14 on which the two side bars 12 and 13 are mounted is provided with a projecting portion 17 on which at least one, and generally two beams 18 and 19 are mounted in rotary manner for constituting respective support bases for the two lower limbs of the patient. Each of the beams 18 and 19 is rotatably mounted on the projecting portion 17 by means of a ball-and-socket joint 20 or 21 in association with locking means 50. The opposite end 22 or 23 of each beam furthest from the end which is rotatably mounted by means of the ball-and-socket joint on the projecting portion of the base carries means 24 or 25 for supporting and holding one of the patient's feet, said means being essentially constituted by a support rod 26 or 27 with a kind of boot 28 or 29 mounted on the end thereof. Each boot serves to imprison a foot, e.g. by means of straps. Each rod 26 or 27 is connected to the end 22 or 23 of the corresponding beam 18 or 19 by fixing lugs 30 or 31 which advantageously constitute deformable parallelograms, with the ends of the lugs being pivotally mounted respectively on the beams and on the support rods 26 or 27. These means are well-known per se and are commonly used in prior art orthopedic operating tables. They are therefore not described in greater detail herein.

In addition, a leg support 32 is mounted between the two ends of each beam. Leg support may be constituted, for example, by a trough-shaped portion 33 which is fixed to a rod 34 which is itself fixed to a sleeve 36 capable of sliding along the corresponding beam 18 or 19 and capable, as above, of being locked by any appropriate means in a determined position between the two ends of the beam, so that the trough 33 whose groove is suitable for receiving the leg of the patient may be situated at a position chosen by the surgeon for the purpose of properly supporting and holding the limb on which the operation is to be performed.

Figure 5:
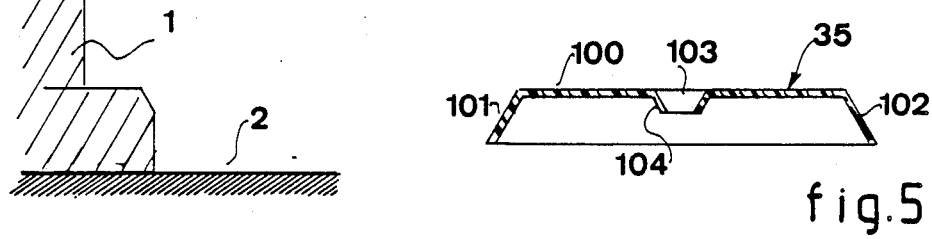
FIG. 5 is a section view through the pelvis support which constitutes one of the component parts of the FIG. 1 orthopedic operating table.
Figure 6:
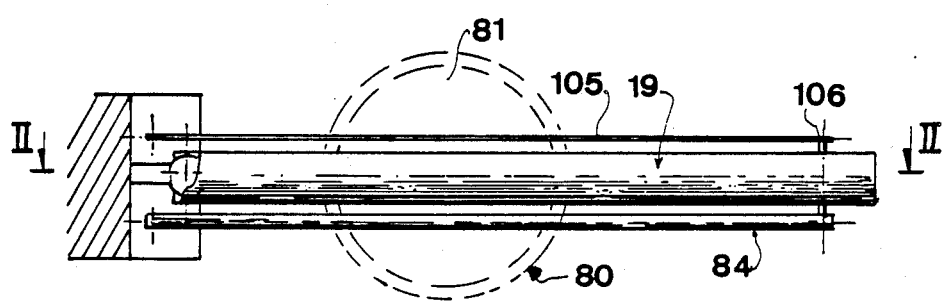
FIG. 6 shows another embodiment of one of the structural members of a beam for the FIG. 1 table.

Further, the end 16 of the base 4 includes a pelvis support 35 whose advantageous shape is described below, in particular with reference to FIG. 5. The pelvis support is situated projecting from the base 4 on the same side as the space containing the two beams 18 and 19 so as to be situated substantially over the two beams with the two beams and said pelvis support thus being situated on the same side of a plane perpendicular to the ground 2 and passing substantially through the two centers of rotation of the ball-and-socket joints 20 and 21. The pelvis support 35 is connected to the base 4 by a fixing lug 36 suitable for offsetting it relative to said base and obtaining the above-defined position. The pelvis support may include an abutment 37 for defining the position of the crutch of the patient whose pelvis is supported by the pelvis support 35 and whose trunk is supported by the flaps 7 and 8.

Naturally, such an operating table could include other conventional auxiliary elements that are commonly used for such operations.

In accordance with a characteristic of the present invention, the two ball-and-socket joints 20 and 21 associated with the two beams 18 and 19 are situated on the projecting portion 17 so as to be contained in a substantially horizontal plane very close to the plane containing the pelvis support and the plane passing through the two flaps 7 and 8 suitable for supporting the patient's trunk. Between their two ends, the beams are constituted by rectilinear beam members which are advantageously of the shape shown in FIG. 2.

Figure 2:
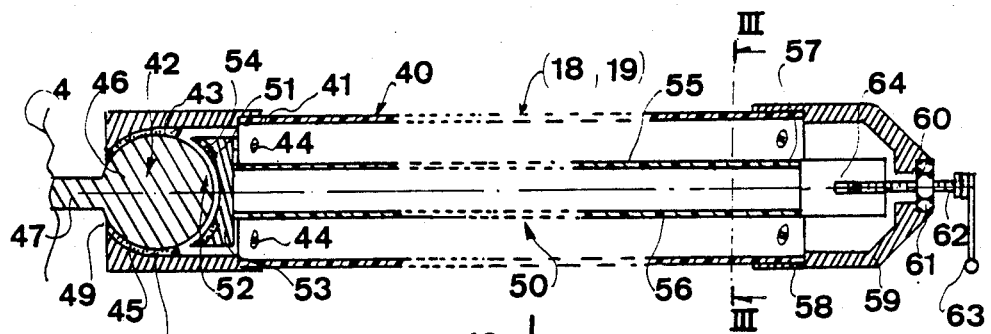
FIG. 2 is a diagrammatic fragmentary section through one embodiment of a beam used in constituting the FIG. 1 table, said section being taken on II—II of FIG. 6.

FIG. 2 shows one of the two beams 18 and 19 of FIG. 1 in fragmentary longitudinal section and by way of example, and it should be understood that both beams are advantageously of the same structure. A beam 18 or 19 is thus constituted by a central portion in the form of a hollow cylindrical tube 40 made of a material which is transparent to the radiation used in radiography. When using X-rays, the material may be constituted, for example, by a braided carbon fiber composite assembled in such a manner as to form a hollow cylindrical tube.

At a first end 41, the tubular portion 40 includes means for forming a ball-and-socket joint 42. These means comprise and end piece 43 fixed to the end 41 of the tubular portion, for example by means of pegs 44, said end piece 43 being shaped on the inside to have a concave hemispherical portion 45 suitable for co-operating with a complementary convex spherical portion 46 which in turn has a portion fixed to the base 4, e.g. by means of a lug 47. Between these male and female spherical portions 46 and 45, means 48 may be disposed in order to encourage friction therebetween. The female portion 45 forms a half-socket including an opening through which the connecting lug 47 of the male portion passes to engage the base 4. The tube 40 can thus pivot through a solid angle of some value which is represented diagrammatically in FIG. 4 by the lines referenced 83, thereby enabling a leg to be positioned relative to the trunk at any such solid angle, for the purpose of facilitating surgical operation.

Naturally, when the beam has taken up the position desired by the surgeon, it is suitable for being locked in said position by locking means 50. In an advantageous embodiment, these locking means 50 comprise a brake shoe 51 disposed in the proximity of the head 52 of the male spherical portion 45, said brake shoe being constituted by a solid portion 53 including a well-known brake material encouraging friction on its face 54 facing the head 52, with the material used for brake linings for automobiles being suitable.

The shoe 51 is mounted at one of the ends of a rod 55 constituted by a hollow cylindrical tube 56 which is also made of a material which is transparent to the radiation used in radiography. The other end 57 of this inner tube 56 emerges from the end 58 of the tubular portion 40 of the beam opposite from the end 41. Thereby making it possible to act on said emerging end in order to move the brake shoe and cause it to come either into contact with the head 52 of the male spherical portion 46, or else to take up a position at a distance therefrom.

The means for controlling displacement of said rod 55 are constituted by a second end fitting 59 fixed to the end 58 of the tubular portion 40 and comprising an opening 60 in which a screw thread 61, for example, is fixed receiving, in turn, a screw 62 suitable for being controlled by a handle 63. The screw 62 co-operates with the end portion 64 of the rod 55 so that when the handle 63 is turned, the end of the screw 62 moves away from or towards the end of the rod 55 as determined by the screw thread 61, thereby causing the head 52 to move towards or away from the male spherical portion. The ball-and-socket joint can thus be locked by setting up high pressure against the brake shoe with the locking being enhanced by the nature of the material 54, or else it may be released in order to change and adjust the orientation of the beam 18 or 19. The beam is locked by applying traction to the tubular portion 40 relative to the inner tube 55, thereby firmly clamping the convex spherical portion 46 between the concave spherical portion 45 and the brake shoe 53.

The means for moving the brake rod 55 in translation are described merely by way of an example of one possible embodiment, however it is obvious that other means could be used for providing the required movement.

Figure 3:
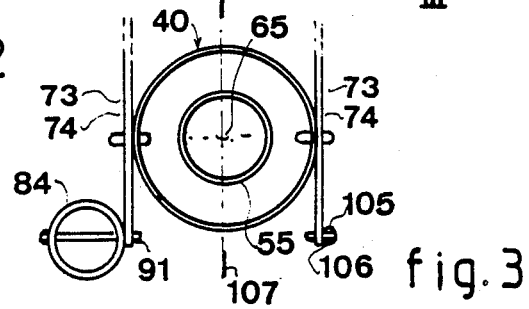
FIG. 3 is a cross-section through the FIG. 2 beam on III—III of FIG. 2.

Reference is now made more particularly to FIG. 3 which is a cross-section through a beam in the position referenced III—III in FIG. 2, with said figure illustrating the fact that the two circularly cylindrical tubular portions 40 and 55 are centered on a common axis 65. Although the material in which the cylinders are made is a material which is transparent to radiographic radiation, as mentioned above, the radiation emitted by the radiation source still has to pass through four wall thicknesses prior to reaching the injured limb and being received by the receiver 82. However, the configuration of the beam makes it possible for the walls to be constantly perpendicular to the radiation, and their thickness is very small. The amount of radiation absorbed is thus practically nil. Further, it should be observed that although the beams are made of a material which is very thin, they are nevertheless adequately stiff by virtue of their cylindrical tubular shape.

Figure 4:
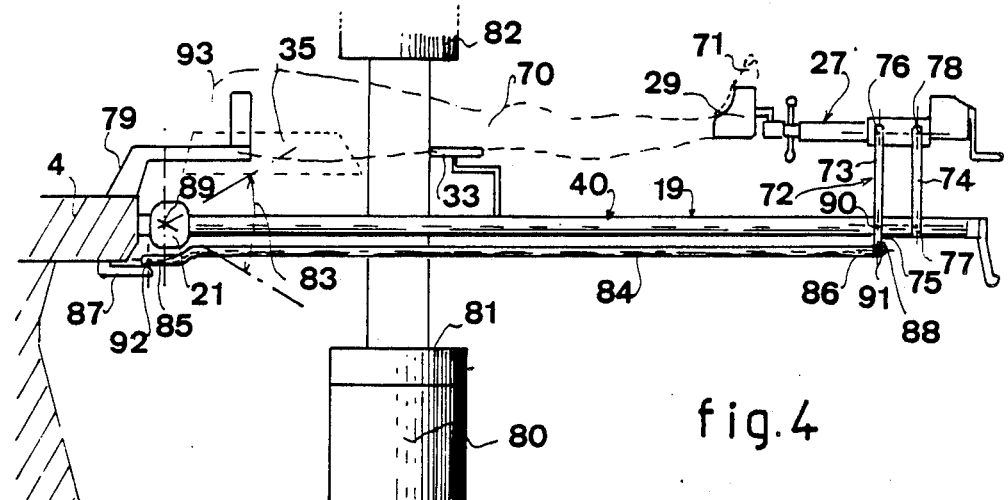
FIG. 4 is a diagrammatic side view of a portion of the orthopedic operating table of FIG. 1, enabling its structure and advantages to be explained.

The X-ray source as shown in FIG. 4 can thus be placed beneath the beam relative to the leg of the patient without the beam being detrimental to the quality of the radiographic image. The same would apply if the organization of the operating theater made it preferable to dispose the radiographic image receiver in the space between the beams and the ground with the source of radiation then being situated above the leg of the patient. With the beam characteristics mentioned above, either configuration makes it possible to obtain a set of elements constituting said operating table and occupying minimum bulk. The surgeon can thus work under optimum conditions of working comfort without being hindered in any way by these elements.

FIG. 4 is a diagram of a portion of the FIG. 1 operating table seen in side view, and more precisely of the portion including the beam 19. The leg 70 of the patient may be positioned, relative to said beam, so that the foot 71 is disposed in the boot means 29 mounted on the rod 27. The rod 27 is mounted parallel to the cylindrical portion 40 by means of a deformable parallelogram 72 constituted by at least two rods 73 and 74 (and in fact generally by four rods) which are pivotally mounted at both of their ends 75, 76 - 77, 78 respectively to the beam 19 (and more particulary the portion 40 thereof), and to the rod 27. Since the two rods 73 and 74 are parallel and are of the same length between their axes of rotation on these two elements respectively, when either of them is moved angularly relative to the beam 40 and the rod 27, then the beam and the rod remain parallel.

In accordance with an important characteristic of the invention, the axis of rotation of each beam is as close as possible to the seat of the pelvis 35, i.e. to the point of the patient's body where the leg joins the trunk. In this way, when the surgeon needs to change the orientation of the leg within relatively small amplitude limits, it is only necessary to act on the beam without altering the adjustment of the lugs 73 and 74 and the foot support 29, since under such circumstances the apparatus does not exert detrimental traction on the leg and the deformation of the parallelogram 72 is sufficient for keeping the leg properly aligned.

Further, when they are in the horizontal position, the plane of the beams substantially coincides with the plane of the base and is very close to that of the flaps 7 and 8 and of the pelvis support 35, and the space lying between the beams and the ground 2 on which the table stands via its stand 1 is very large. This makes it possible to position, for example, an X-ray source 80 in said space with its emitting surface 81 very close to the leg 70. As mentioned above, although a beam is interposed between the radiation source and the leg, by virtue of its small wall thickness and the nature of the material constituting the walls, the beam does not constitute an obstacle preventing good-quality images being obtained at a receiver 82 placed facing the emission surface of the source.

As described above, the deformable parallelogram 72 enables the rod 27 to be maintained permanently parallel to the beam. However, as also mentioned above, the surgeon may need to change the orientation of the leg relative to the plane of the base 4. To do this, the surgeon may unlock the brake shoe 53 as explained with reference to FIG. 2, e.g. using the handle 63, and then orient the beam 19 in the appropriate direction within the solid angle outlined at 83. The rod 27 is kept parallel with the beam by virtue of the above-described deformable parallelogram 72. However, if the leg orientation is changed a great deal, the rod 27 may apply traction or compression forces on the leg, and these forces may be dangerous. In order to avoid such forces being set up, the orthopedic operating table also includes a control ink 84 pivotally mounted at its two ends 85 and 86 respectively to a portion 87 of the base 4 and to a projecting portion 88 of the lug 73 of the parallelogram 72, so that the following points of rotation are located substantially on the vertices of a trapezium: 89 for the beam ball-and-socket joint; 90 for the lug 73 on the beam 19; 91 for the link 84 on the projecting portion 88 of the lug 73; and 92 for the link 84 on the base 4.

As mentioned above, the point of rotation 89 of the ball-and-socket joint cannot exactly coincide with the point of rotation of the leg 70 relative to the pelvis 93 on the pelvis support 35. Thus, when the beam 19 needs to be pivoted relative to the base 4, any variations in the distance between the pelvis 93 and the foot-retaining means 71 may be compensated by the axis of rotation 92 of the link 84 on the base 4 being slightly rearwardly offset, i.e. towards the stand 1, so that the distance between the two axes 91 and 92 is greater than the distance between the two axes 89 and 90. Thus, when the beam is rotated upwardly, the foot support means 71 remains at a substantially constant distance from the pelvis support. The link 84 is then pulling on the lug 73 in order to cause its end 76 to rotate slightly clockwise away from the pelvis support 35 so as to compensate for the opposite-direction movement due to the beam rotating about the ball-and-socket joint.

Similarly, when the beam 19 is rotated clockwise, i.e. towards the ground, the lug 73 is rotated anticlockwise so as to compensate for the tendency of the foot support means to move away from the pelvis support, thereby ensuring that their distance apart remains substantially constant in this case also.

In accordance with another characteristic of the invention, the pelvis support 35 is situated between two vertical planes passing respectively through the point of rotation 89 of the beam 19 relative to the base 4 and through the foot 71 of the patient, such that the pelvis support may be brought into the radiation field of the X-ray source. The support 35 is likewise made of a material which is transparent, in particular to X-rays, for example a carbon fiber composite. The patient's pelvis can rest on the pelvis support and can be continuously X-rayed thereon. This characteristic thus makes it possible to perform operations on the hip or to reduce fractures of the pelvis under continuous x-ray monitoring.

In order to avoid the pelvis support from deforming in spite of it supporting a relatively large weight, it is made in such a manner as to be relatively rigid. As shown in FIG. 5, it may be constituted by a thin wall 100 shaped to receive the pelvis of the patient but reinforced laterally by sides 101 and 102, and also pierced substantially in its middle by an opening 103 which is likewise surrounded by sides 104, with said sides 101, 102, and 104 extending obliquely relative to the normal to the wall 100 so that the thickness of the support taken in a direction parallel to said normal is small at all points.

A link 84, as described above, running parallel to the beam 18 or 19 is used for controlling the deformation of parallelogram 72, as described above. However, in order to prevent it from hindering the transmission of radiographic radiation between the source and the leg, the link is offset sideways relative to the tubular portion 40 so that the link and the beam are situated on opposite sides of a plane normal to the ground 2 and tangential to at least one of these two items. In particular, this plane may be the plane containing the lug 73 and may extend parallel to the beam 19, with the link 84 and the tubular portion 40 thus being situated on opposite sides of the lug 73.

Since the link 84 transmits force to the end 23 of the tubular portion 40 via the projecting portion 88 of the lug 73, it tends to deform into an arc of a circle and the middle of the link tends to press against the wall of the tubular portion 40 which would contribute to increasing the thickness of material to be passed through in the vertical direction by the radiographic radiation, and in particular by X-rays.

In order to avoid this drawback, each link 84 is associated with a side-draw-bar 105. In order to provide better equilibrium for the support rod 27, and thus for the foot support means 29, each lug 73 and 74 is advantageously constituted by two lugs which are symmetrically disposed relative to the longitudinal plane 107 passing through the central axis 65 of the beam. In this case, the link is rotatably mounted to one of the two lugs 73 and the draw-bar is mounted on the other one of the lugs 73 and bears against a point 106 of said other lug 73 which is symmetrical about the vertical plane 107 to the point of rotation 91 defined above. The other end of the draw-bar is rotatably mounted on the portion 87 of the base 4 at a point which is symmetrical about the same plane 107 to the point of rotation 92 of the link. In this way, the four fixing points of the link and the draw-bar constitute a rectangle capable of deforming, for the most part elastically, under the effect of the stress exerted by displacing the beam, thereby preventing the link from deforming as described above.

The table described undoubtedly possesses numerous advantages in its structure and in the nature of some of its component parts, such as the beams and the pelvis support. In particular, it enables a surgeon to operate on and/or reduce fractures of the lower limbs and of the pelvis while benefitting from continuous radiographic monitoring, with the beams and the pelvis support being made of a material which is transparent to radiographic radiation. The structural shapes of the main components ensures that they are very stiff and strong in spite of being thin-walled. Further, since the source of radiation or the radiographic image receiver is suitable for being disposed between the plane of the beams and the ground, and since the planes of the various items such as the base, the flaps, the pelvis support, and the beams when in the horizontal position are all very close to one another, the overall bulk of the table is kept to a minimum and the surgeon's work is greatly facilitated. The surgeon may have very easy access to all of the functional means which are useful for operating in conjunction with continuous radiographic monitoring. Operations may be performed more reliably and more quickly, which is an important objective for patient well-being.

I claim:

1. An orthopedic operating table for the limbs of a person, in particular the lower limbs, the table having a source of radiographic radiation and a radiographic image receiver in juxtaposition thereto and comprising:

a stand suitable for being positioned on the ground;

a base mounted on the top of said stand;

at least one flap for supporting the trunk of said person;

support means for attaching said flap to one side of said base so that said flap is offset relative to said base;

at least one beam comprising a central portion having a first end and a second end, said central portion being in the form of a hollow circularly cylindrical tube made of a material which is transparent to radiographic radiation emitted by a radiation source;

means for pivotally mounting said beam to said base in the proximity of the point where said limb joins the trunk of the person, to the other side of the base opposite to the side on which the support means for said flap are disposed with the distance between said beam when in a position substantially parallel to said ground on which said stand is suitable for being positioned, and said beam being greater in height than the height of one of said source of radiographic radiation and said radiographic image receiver from said ground, said means for pivotally mounting said beam to said base comprising a projecting portion fixed to said base and a ball-and-socket joint having a male portion constituted by a convex spherical portion fixed to said projecting portion of the base by a connection lug, and a female portion constituted by an end piece fixed to said first end of said beam, the inside of said end piece being shaped in the form of a complementary concave hemispherical portion forming a half-cup including an opening through which said connection lug passes; and controllable locking means for locking said ball-and-socket joint in a determined position and constituted by a brake shoe disposed in the proximity of the convex portion and including friction material on a face thereof facing the convex portion, a transmission rod constituted by a circularly cylindrical hollow tube made of a material transparent to the radiographic radiation having a first end of said rod cooperating with said shoe and a second end emerging from the second end of the tubular portion of said beam, and means for controlling the displacement of said transmission rod relative to said tubular portion forming said beam.

2. A table according to claim 1, wherein the ball-and-socket joint includes friction-increasing means between said concave and convex spherical portions for increasing the friction therebetween.

3. A table according to claim 1, wherein said source of radiation is an X-ray source, and said material which is transparent to said radiation is a braided carbon fiber composite.

4. An orthopedic operating table according to claim 1, wherein said beam comprises, at said second end means for supporting and holding a foot of the patient, said means for supporting comprising a support rod, a boot fixed to one end of said rod and suitable for imprisoning a foot of the patient, and a deformable parallelogram connecting said rod to said beam, said parallelogram being constituted by fixing lugs, with the ends of said lugs being pivotally mounted respectively on said second end of said beam and on said support rod.

5. A table according to claim 4, further including a draw-bar connected to said base and to said beam, with a length of said draw-bar between its connection points with said base and said beam being substantially equal to the length of said link, said draw-bar being situated substantially in a plane perpendicular to said ground passing through a longitudinal axis of said beam to the plane passing through a longitudinal axis of said link. perpendicularly to said ground.

6. An orthopedic operating table according to claim 1, further comprising:

a pelvis support situated in a half-space delimited by a plane passing through the point of rotation of said beam and substantially perpendicularly to the ground on which said stand is suitable for being positioned, and including said beam, said pelvis support being constituted by a thin wall shaped to receive the pelvis of a patient, said thin wall being laterally reinforced by thin sides extending obliquely relative to the normal of said wall and said pelvis support being made of a material which is transparent to radiographic radiation.

7. A table according to claim 6, wherein said source of radiation is an X-ray source, and said material which is transparent to said radiation is a braided carbon fiber composite.

8. A table according to claim 2, wherein said source of radiation is an X-ray source, and said material which is transparent to said radiation is a braided carbon fiber composite.

9. An orthopedic operating table according to claim 4, further comprising:

a control link for controlling said deformable parallelogram, said control link being pivotally mounted at opposite ends respectively on a portion of said base and on a projecting portion of a lug mounted on the beam forming said parallelogram, such that points of rotation of said ball-and-socket joint, of the lug on the beam, of the link on the lug, and of the link on the base lie on vertices of a trapezium, with the length of said control link between said two points of rotation being greater than the length of said beam between said two points of rotation, and said link and the tubular portion constituting the beam being situated on either side of a plane substantially perpendicular to said ground on which said stand is suitable for being positioned.

* * * * *